United States Patent
Yde et al.

(10) Patent No.: US 10,093,894 B2
(45) Date of Patent: Oct. 9, 2018

(54) METHOD FOR OPTIMIZING A PROCESS FOR FREEZE DRYING A BACTERIA-CONTAINING CONCENTRATE

(71) Applicant: Chr. Hansen A/S, Hoersholm (DK)

(72) Inventors: Birgitte Yde, Stenloese (DK); Tania Ivanova Georgieva, Hoersholm (DK); Anders Clausen, Virum (DK); Susanne Abrahamsen, Karslunde (DK)

(73) Assignee: Chr. Hansen A/S, Hoersholm (DK)

( * ) Notice: Subject to any disclaimer, the term of this patent is extended or adjusted under 35 U.S.C. 154(b) by 0 days.

(21) Appl. No.: 14/421,385

(22) PCT Filed: Aug. 20, 2013

(86) PCT No.: PCT/EP2013/067282
§ 371 (c)(1),
(2) Date: Feb. 12, 2015

(87) PCT Pub. No.: WO2014/029758
PCT Pub. Date: Feb. 27, 2014

(65) Prior Publication Data
US 2015/0232801 A1    Aug. 20, 2015

(30) Foreign Application Priority Data

Aug. 20, 2012 (DK) ................................ 2012 00513
Dec. 21, 2012 (DK) ................................ 2012 00821
Feb. 20, 2013 (DK) ................................ 2013 00101

(51) Int. Cl.
*C12N 1/04* (2006.01)

(52) U.S. Cl.
CPC ..................... *C12N 1/04* (2013.01)

(58) Field of Classification Search
None
See application file for complete search history.

(56) References Cited

U.S. PATENT DOCUMENTS

| 4,217,419 | A | 8/1980 | Suzuki |
| 9,308,271 | B2 | 4/2016 | Yde et al. |
| 9,493,737 | B2 | 11/2016 | Georgieva et al. |
| 2015/0218507 | A1 | 8/2015 | Georgieva et al. |
| 2015/0232801 | A1 | 8/2015 | Yde et al. |

FOREIGN PATENT DOCUMENTS

| CN | 101323850 | 12/2008 |
| CN | 101711746 | 5/2010 |
| CN | 102145020 | 8/2011 |
| CN | 102283803 | 12/2011 |
| WO | WO2009/092703 | 7/2009 |
| WO | WO-2012/076665 | 6/2012 |
| WO | WO-2012/088261 | 6/2012 |
| WO | WO 2013/083762 | * 2/2013 |
| WO | WO 2013/024178 | * 6/2013 |

OTHER PUBLICATIONS

Coulibaly et al. (International Journal of Microbiology, vol. 2010, Article ID 625239, pp. 1-9).*
Savini et al., Nutrients 2010, 2, 330-339.*
Jafar et al., "Analysis of Heat and Mass Transfer in Freeze Drying," Drying Technology: An International Journal, vol. 21, No. 2, pp. 249-263, 2003.
Pikal et. al, "The collapse temperature in freeze drying: Dependence on measurement methodology and rate of water removal from the glassy phase," International Journal of Pharmaceutics, No. 62, pp. 165-186, Jul. 1990.
Schersch et al., "Systematic Investigation of the Effect of Lyophilizate Collapse on Pharmaceutically Relevant Proteins I: Stability after Freeze-Drying," J. Pharm. Sci., vol. 99, No. 5, pp. 2256-2278, May 2010.
Zhao et al., "Effect of protective agents, freezing temperature, rehydration media on viability of malolactic bacteria subjected to freeze-drying," Journal of Applied Microbiology, No. 99, pp. 333-338, Aug. 2005.
Zhao et al., "Influence of freeze-drying conditions on survival of *Oenococcus oeni* for malolactic fermentation," International Journal of Food Microbiology, No. 135, pp. 64-67, Sep. 2009.
International Search dated Oct. 24, 2013 issued in PCT/EP2013/067282.
Office Action dated Feb. 15, 2018 in U.S. Appl. No. 14/421,328 (US 2015-0218507).
Restriction Requirement issued in co-pending U.S. Appl. No. 14/421,328, dated Sep. 21, 2016 (US 2015/0218507).
Non-Final Office action issued in co-pending U.S. Appl. No. 14/421,328, dated Apr. 21, 2017 (US 2015/0218507).
Non-Final Office action in co-pending U.S. Appl. No. 14/421,328, dated Jun. 1, 2017 (US 2015/0218507).
International Search Report dated Oct. 24, 2013 issued in PCT/EP2013/067338.

* cited by examiner

*Primary Examiner* — Irene Marx
(74) *Attorney, Agent, or Firm* — Foley & Lardner LLP

(57) ABSTRACT

The present invention relates to a process for optimizing the storage stability of a freeze dried bacteria-containing product obtained from a bacteria-containing concentrate, wherein the process is carried out at a pressure which will provide a sublimation temperature which is at least 10° C. above the melting point of the frozen bacteria-containing concentrate. Further, the present invention relates to the freeze dried concentrates per se.

16 Claims, 4 Drawing Sheets

Figure 5

Steam table (Saturation Condition)   0.001-1000 mbar

Figure 1:
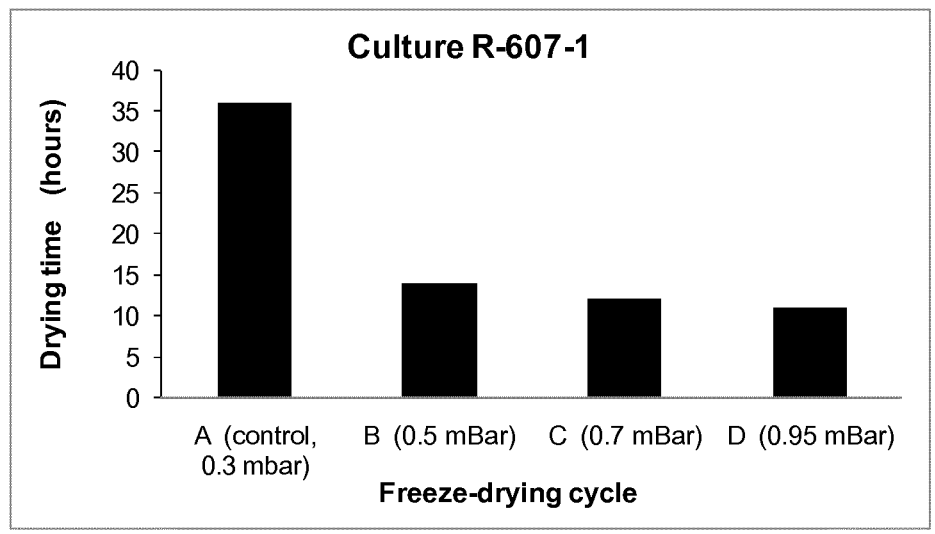

| P mbar | p Torr | t °C | v m³/kg | h kJ/kg | r kJ/kg | P mbar | p Torr | t °C | v m³/kg | h kJ/kg | r kJ/kg |
|---|---|---|---|---|---|---|---|---|---|---|---|
| 0.001 | 0.00075 | -76.26 | 908600 | 2361 | 2832 | 40 | 30.00 | 28.97 | 34.82 | 2554 | 2433 |
| 0.005 | 0.00375 | -65.55 | 191600 | 2380 | 2835 | 42 | 31.50 | 29.82 | 33.25 | 2556 | 2431 |
| 0.01 | 0.0075 | -60.56 | 98110 | 2389 | 2836 | 44 | 33.00 | 30.63 | 31.82 | 2557 | 2429 |
| 0.02 | 0.0150 | -55.34 | 50260 | 2399 | 2837 | 46 | 34.50 | 31.41 | 30.51 | 2559 | 2427 |
| 0.03 | 0.0225 | -52.17 | 33990 | 2405 | 2838 | 48 | 36.00 | 32.17 | 29.31 | 2560 | 2426 |
| 0.04 | 0.0300 | -49.87 | 25760 | 2409 | 3838 | 50 | 37.50 | 32.89 | 28.20 | 2562 | 2424 |
| 0.05 | 0.0375 | -48.04 | 20780 | 2412 | 2838 | 55 | 41.25 | 34.60 | 25.78 | 2565 | 2420 |
| 0.06 | 0.0450 | -46.53 | 17430 | 2415 | 2838 | 60 | 45.00 | 36.18 | 23.74 | 2568 | 2416 |
| 0.07 | 0.0525 | -45.23 | 15030 | 2418 | 2838 | 65 | 48.75 | 37.65 | 22.02 | 2570 | 2413 |
| 0.08 | 0.0600 | -44.11 | 13210 | 2420 | 2838 | 70 | 52.50 | 39.02 | 20.53 | 2573 | 2409 |
| 0.09 | 0.0675 | -43.08 | 11800 | 2422 | 2838 | 75 | 56.25 | 40.32 | 19.24 | 2575 | 2406 |
| 0.1 | 0.075 | -42.18 | 10660 | 2423 | 2838 | 80 | 60.00 | 41.54 | 18.10 | 2577 | 2403 |
| 0.2 | 0.150 | -36.03 | 5472 | 2435 | 2839 | 85 | 63.76 | 42.69 | 17.10 | 2579 | 2401 |
| 0.3 | 0.225 | -32.24 | 3706 | 2442 | 2839 | 90 | 67.51 | 43.79 | 16.20 | 2581 | 2398 |
| 0.4 | 0.300 | -29.51 | 2811 | 2447 | 2838 | 95 | 71.26 | 44.84 | 15.40 | 2583 | 2395 |
| 0.5 | 0.375 | -27.31 | 2269 | 2451 | 2838 | 100 | 75.01 | 45.84 | 14.67 | 2585 | 2393 |
| 0.6 | 0.450 | -25.51 | 1905 | 2454 | 2838 | 110 | 82.51 | 47.71 | 13.41 | 2588 | 2389 |
| 0.7 | 0.525 | -23.99 | 1643 | 2457 | 2838 | 120 | 90.01 | 49.45 | 12.36 | 2591 | 2384 |
| 0.8 | 0.600 | -22.63 | 1445 | 2459 | 2838 | 130 | 97.51 | 51.07 | 11.46 | 2594 | 2380 |
| 0.9 | 0.675 | -21.40 | 1291 | 2461 | 2838 | 140 | 105.0 | 52.58 | 10.69 | 2597 | 2377 |
| 1 | 0.75 | -20.33 | 1167 | 2463 | 2838 | 150 | 112.5 | 54.00 | 10.02 | 2599 | 2373 |
| 2 | 1.50 | -12.91 | 600.5 | 2477 | 2837 | 160 | 120.0 | 55.34 | 9.433 | 2602 | 2370 |
| 3 | 2.25 | -8.37 | 407.3 | 2485 | 2836 | 170 | 127.5 | 56.62 | 8.911 | 2604 | 2367 |
| 4 | 3.00 | -5.05 | 309.3 | 2491 | 2835 | 180 | 135.0 | 57.83 | 8.445 | 2606 | 2364 |
| 5 | 3.75 | -2.41 | 249.9 | 2496 | 2835 | 190 | 142.5 | 58.98 | 8.027 | 2608 | 2361 |
| 6 | 4.50 | -0.21 | 209.9 | 2500 | 2834 | 200 | 150.0 | 60.09 | 7.650 | 2610 | 2359 |
| 7 | 5.25 | 1.89 | 181.32 | 2505 | 2497 | 210 | 157.5 | 61.14 | 7.308 | 2612 | 2356 |
| 8 | 6.00 | 3.77 | 159.74 | 2509 | 2493 | 220 | 165.0 | 62.16 | 6.996 | 2614 | 2353 |
| 9 | 6.75 | 5.45 | 142.82 | 2512 | 2489 | 230 | 172.5 | 63.14 | 6.710 | 2615 | 2351 |
| 10 | 7.50 | 6.98 | 129.21 | 2514 | 2485 | 240 | 180.0 | 64.08 | 6.448 | 2617 | 2349 |
| 11 | 8.25 | 8.38 | 118.02 | 2517 | 2482 | 250 | 187.5 | 64.99 | 6.206 | 2618 | 2346 |
| 12 | 9.00 | 9.67 | 108.67 | 2519 | 2479 | 260 | 195.0 | 65.87 | 5.982 | 2620 | 2344 |
| 13 | 9.75 | 10.87 | 100.73 | 2522 | 2476 | 270 | 202.5 | 66.72 | 5.774 | 2621 | 2342 |
| 14 | 10.60 | 11.99 | 93.90 | 2524 | 2473 | 280 | 210.0 | 67.54 | 5.580 | 2623 | 2340 |
| 15 | 11.25 | 13.04 | 87.96 | 2526 | 2471 | 290 | 217.5 | 68.34 | 5.400 | 2624 | 2338 |
| 16 | 12.00 | 14.03 | 82.75 | 2527 | 2468 | 300 | 225.0 | 69.12 | 5.231 | 2626 | 2336 |
| 17 | 12.75 | 14.97 | 78.14 | 2529 | 2466 | 320 | 240.0 | 70.61 | 4.924 | 2628 | 2333 |
| 18 | 13.50 | 15.86 | 74.03 | 2531 | 2464 | 340 | 255.0 | 72.02 | 4.652 | 2630 | 2329 |
| 19 | 14.25 | 16.70 | 70.34 | 2532 | 2462 | 360 | 270.0 | 73.37 | 4.409 | 2633 | 2328 |
| 20 | 15.00 | 17.51 | 67.01 | 2534 | 2460 | 380 | 285.0 | 74.65 | 4.191 | 2635 | 2322 |
| 21 | 15.75 | 18.28 | 64.00 | 2535 | 2458 | 400 | 300.0 | 75.88 | 3.995 | 2637 | 2319 |
| 22 | 16.50 | 19.03 | 61.24 | 2536 | 2457 | 420 | 315.0 | 77.08 | 3.818 | 2839 | 2316 |
| 23 | 17.25 | 19.74 | 58.72 | 2538 | 2455 | 440 | 330.0 | 78.19 | 3.653 | 2641 | 2313 |
| 24 | 18.00 | 20.43 | 56.41 | 2539 | 2453 | 460 | 345.0 | 79.27 | 3.504 | 2643 | 2311 |
| 25 | 18.75 | 21.09 | 54.28 | 2540 | 2452 | 480 | 360.0 | 80.32 | 3.367 | 2644 | 2308 |
| 26 | 19.50 | 21.73 | 52.30 | 2541 | 2450 | 500 | 375.0 | 81.34 | 3.241 | 2646 | 2305 |
| 27 | 20.25 | 22.35 | 50.47 | 2542 | 2449 | 550 | 412.5 | 83.73 | 2.964 | 2650 | 2299 |
| 28 | 21.00 | 22.95 | 48.77 | 2544 | 2447 | 600 | 450.0 | 85.95 | 2.732 | 2654 | 2294 |
| 29 | 21.75 | 23.53 | 47.18 | 2545 | 2446 | 650 | 487.5 | 88.02 | 2.535 | 2657 | 2288 |
| 30 | 22.50 | 24.09 | 45.69 | 2546 | 2445 | 700 | 525.0 | 89.96 | 2.365 | 2660 | 2283 |
| 32 | 24.00 | 25.17 | 42.99 | 2548 | 2442 | 750 | 562.5 | 91.78 | 2.217 | 2663 | 2279 |
| 34 | 25.50 | 26.19 | 40.59 | 2549 | 2440 | 800 | 600.0 | 93.51 | 2.087 | 2666 | 2274 |
| 36 | 27.00 | 27.16 | 38.46 | 2551 | 2437 | 850 | 637.6 | 95.15 | 1.972 | 2668 | 2270 |
| 38 | 28.50 | 28.09 | 36.55 | 2553 | 2435 | 900 | 675.1 | 96.71 | 1.869 | 2671 | 2266 |
| | | | | | | 950 | 712.6 | 98.20 | 1.777 | 2673 | 2262 |
| | | | | | | 1000 | 750.1 | 99.63 | 1.694 | 2675 | 2258 |

METHOD FOR OPTIMIZING A PROCESS FOR FREEZE DRYING A BACTERIA-CONTAINING CONCENTRATE

CROSS REFERENCE TO RELATED APPLICATIONS

The present application is the U.S. National Stage of International Application No. PCT/EP2013/067282, filed on Aug. 20, 2013, and claims priority to Danish Patent Application No. 201200513, filed on Aug. 20, 2012, Danish Patent Application No. 201200821, filed on Dec. 21, 2012, and Danish Patent Application No. 201300101, filed on Feb. 20, 2013.

The present invention relates to a process for optimizing the storage stability of a freeze dried bacteria-containing product obtained from a bacteria-containing concentrate, wherein the process is carried out at a pressure which will provide a sublimation temperature which is at least 10° C. above the melting point of the frozen bacteria-containing concentrate. Further, the present invention relates to the freeze dried concentrates per se.

BACKGROUND OF THE INVENTION

Before inoculation into products, such as food products or dietary supplements, bacteria are cultured in order to provide a suspension containing large amounts of bacteria. The suspension is usually concentrated using centrifugation, filtration, distillation, sedimentation or flocculation. This concentration step is often followed by freezing or freeze-drying or drying or storage of the microbial concentrate as a frozen product in liquid nitrogen to preserve and/or store the bacteria.

However, freeze-drying of the bacteria is a bottleneck in the industrial production of storable viable bacteria due to the cell damage and loss of viable cells during the freeze-drying but also due to the long process time, usually days, thus resulting in high cost industrial freeze drying processes. This is primary due to the primary drying, or ice sublimation, stage of freeze drying process which is frequently the most time consuming portion of the process (PIKAL M. J.; SHAH S.). This is due to the practice to keep the products at a low product temperature during primary freeze-drying in order to avoid product collapse i.e. loss in particle microstructure which is regarded as determinable for products quality and stability (Schersch et al. 2256-78). Product collapse is usually avoided commercially by applying mild process conditions i.e. low pressure and low shelf/heating plate temperature during freeze-drying, which results in prolonged drying cycles.

Therefore, there is still a need to improve the efficiency of freeze drying methods suitable for bacteria-containing suspensions, to obtain a highly concentrated bacteria suspension with a limited loss of biological activity as well as a limited loss of viable bacteria both during the production and the subsequent storage. These methods need to be feasible at any scale, but especially on the industrial scale, where large volumes of suspension are concentrated.

SUMMARY OF THE INVENTION

The present inventors have researched intensely in ways to improve the storage stability of a freeze dried bacteria-containing product obtained from a bacteria-containing concentrate, and have now provided a novel process for optimizing the storage stability of a freeze dried bacteria-containing product.

It has surprisingly turned out that it is possible to perform the freeze drying at higher temperature and/or higher pressure than conventionally used, without negative impact on the cell viability, biological activity (acidification or other activity) and water activity of the resulting product, compared to a product produced under conventional conditions. Moreover, the tested more aggressive freeze drying conditions (higher temperature and/or higher pressure) also result in a faster and more efficient drying, and thus in less costly manufacturing process. Further, it has surprisingly been found that the storage stability of the products produced using the processes of the invention is significantly improved.

Thus, in a first aspect, the invention relates to a process for optimizing the storage stability of a freeze dried bacteria-containing product obtained from a bacteria-containing concentrate, the process comprising
  i) preparing a sample of the frozen bacteria-containing concentrate (which optionally contains one or more additives, such as a cryo protectant and/or a stabilizer) and measuring the melting point,
  ii) calculating a freeze drying pressure which will provide a sublimation temperature which is at least 10° C. above the melting point of the frozen bacteria-containing concentrate, and
  iii) freeze drying the bacteria-containing concentrate at a pressure which is at least the calculated freeze-drying pressure until a freeze dried bacteria-containing product having a desired $a_w$ is obtained from the bacteria-containing concentrate.

The process can be used for improving the storage stability of a bacteria-containing freeze dried product obtained from a bacteria-containing concentrate by freeze drying. The process can also be used for improving the viability of bacteria upon preservation by freeze-drying.

In another aspect, the present invention relates to a bacteria-containing product obtainable by a process of the present invention. Preferred freeze-dried products according to the invention contain about $10^9$ to about $10^{13}$ cfu/g.

DETAILED DISCLOSURE

Freeze dried products are expected to have long term storage stability. However, sometimes the products are not as stable as desired and for other products the inventors have experienced that rather small changes in the production affect the storage stability.

The three principle stages of freeze drying are: freezing, primary drying (sublimation) and secondary drying. In other words in standard freeze drying the water goes from ice to vapour without a liquid stage.

This invention is related to the observation that there is a correlation between the physical appearance of the freeze dried pellets when evaluated by microscopy and the storage stability. Surprisingly it was found that there is a correlation between the shininess and the storage stability. It was furthermore found that freeze dried products with high shininess often have higher density than products without shiny appearance. This means that these products are less porous most likely as a result of a micro-collapse during the drying process. A micro-collapse will occur when a small part of the water is in liquid form—which is normally considered unwanted in a freeze drying process. Whether a collapse occurs depends on whether the sublimation temperature is lower than the melting point of the pre-freeze dried product (PFD) in which case micro-collapse normally does not occur.

The present invention provides the possibilities to improve the storage stability of existing products by small changes in drying profile, to be able to predict the storage stability of new products prepared by freeze drying, and to predict if changes in the production process might have a negative effect on storage stability.

Thus, in a first aspect, the present invention relates to a process for optimizing the storage stability of a freeze dried bacteria-containing product obtained from a bacteria-containing concentrate, the process comprising i) preparing a sample of the frozen bacteria-containing concentrate (which optionally contains one or more additives, such as a cryo protectant and/or a stabilizer) and measuring the melting point, ii) calculating a freeze drying pressure which will provide a sublimation temperature which is at least 10° C. above the melting point of the frozen bacteria-containing concentrate, and iii) freeze drying the bacteria-containing concentrate at a pressure which is at least the calculated freeze-drying pressure until a freeze dried bacteria-containing product having a desired $a_w$ is obtained from the bacteria-containing concentrate.

As evident to a person of skill in the art the exact value of the melting point of a frozen bacteria-containing concentrate will depend on the bacterial species, the fermentation procedure, possible washing of the fermentate, the concentration factor, the nature and amount of optional cryo protectant and/or stabilizer etc. Thus, it is necessary to prepare a sample and measure the melting point and thereafter a freeze drying pressure which will provide a sublimation temperature which is at least 10° C. above the melting point of the frozen bacteria-containing concentrate can be calculated.

The calculation is done e.g. by reading a steam table as provided in FIG. 5 and extrapolating as necessary to a value which will provide a sublimation temperature which is at least 10° C. above the melting point of the frozen bacteria-containing concentrate. The temperature difference should be sufficient to provide some melting. According to the results in Example 2 temperature differences of about 14° C. and 17° C. provided good results. A too high temperature difference may make it difficult to dry the bacteria-containing concentrate to a desired $a_w$. It is contemplated that a temperature difference in the range of 10° C. to 30° C., such as in the range of 10° C. to 20° C., e.g. in the range of 12° C. to 18° C., such as the range of 13° C. to 17° C. will provide optimal results.

Generally, the freeze drying is continued until the weight of the bacteria-containing concentrate in the freeze dryer has been stable for at least 1 hour, such as at least 2 hours, preferably at least 3 hours and/or a desired $a_w$ has been obtained, e.g. an $a_w$ which is no more than 0.2, such as 0.1 or 0.15. Often the freeze drying is performed as a two-step process, primary drying and secondary drying as discussed in the following. The calculated freeze drying pressure refers to the pressure to be used in the primary drying.

Freeze drying, also known as lyophilisation, lyophilization, or cryodesiccation, is a dehydration process typically used to preserve a perishable material or make the material more convenient for transport/distribution. Freeze drying works by freezing the material and then reducing the surrounding pressure to allow the frozen water in the material to sublimate directly from the solid phase to the gas phase.

In the present context one may use any suitable freezing. As known—there are several herein relevant suitable freezing methods available to the skilled person, wherein some of these are fast freezing at −196° C. (liquid nitrogen) as the frozen product representing spheres or cylinders in the diameter range of 1 to 15 mm. The bacteria cells could also be frozen slowly by placing the bacterial concentrate on product trays or shelf trays in shelf freeze-dryers and allowing the culture to cool more slowly.

Primary drying refers to that stage where ice is transformed into vapor by sublimation. As evident in the context of the present invention, the pressure is selected so that a small part of the bacteria-containing concentrate will be melted.

Secondary drying refers to that stage where unfrozen water is removed by desorption During freeze-drying, to sublimate ice (primary drying) and to desorpt bound water (secondary drying), it is necessary to supply energy to the sample (i.e. the bacteria-containing concentrate). The situation for samples on trays in the drying chamber depends on whether the product trays are in direct contact with the heating sources, or whether the product trays are suspended between the heating sources without direct contact. In the first case, the sample is heated primary by conduction from the heat sources, whereas in the second case it is heated is by radiation.

In the present context one may use suitable heating source in the freeze-dryer. As known—there are several herein relevant suitable large-scale freeze-dryers available to the skilled person, wherein some of these are commercially available as with radiation heating or conduction heating. In summary, necessary energy can be transduced to the sample in 3 different forms By radiation of heated surface. Drying samples on trays in the freeze-drying chamber is done through the use of radiant heating to the sample and the tray surface.

By conduction from heated plates or gases. Energy transfer is by conductivity, as well by direct contact of the product or product container/tray with the shelfs/heating plate By gas convection Heating plates as described herein may also be seen as:
heating shelfs
shelf heating plates
heating surface shaped as product trays
or as any heating surface giving heat energy to ensure primary and secondary drying.

Heating plate temperature described herein may also be seen as shelf temperature, or any temperature of the heating surface.

Preferably, the pressure that is applied during the freeze-drying step is in the range of 0.2 to 2.0 mBar, such as in the range of 0.5 to 2.0 mBar, 0.5 to 2.0 mBar, more preferably in the range 0.5 to 1.0 mBar, 0.6 to 0.8 mBar, and even more preferably 0.5 to 0.6 mBar. The pressure applied during the freeze-drying step may also be in the range of 0.8 to 1.5 mBar, 0.8 to 1.1 mBar, 0.7 to 1.1 mBar, 0.4 to 0.6 mBar, 0.9 to 1.3 mBar, or 1.0 to 1.9 mBar, or in the range of 0.35 to 0.75 mbar, such as 0.35 to 0.5 mBar. Depending on the formulation. e.g. the cryoprotectant used, also a pressure in the range of 0.2 to 0.35 mBar may be relevant.

The pressure applied during the freeze-drying step is preferably maintained for a certain time period, e.g. for more than 1 hour, more preferably for more than 2, 3, 4, 5, or even more than 7 hours such as 12, 18 or 24 hours. The person of skill in the art will be able to determine the exact period of time depending on the amount of bacteria-containing concentrate to be dried and the temperature profile etc.

The drying process is performed until the $a_w$ is no more than 0.2, such as 0.1 or 0.15.

The bacteria-containing concentrate used in the improved freeze-drying process comprises at least one LAB genus, preferably selected from the group consisting of *Lactococcus, Lactobacillus, Leuconostoc, Carnobacterium, Pediococcus,* and *Streptococcus* and more preferably at least one species selected from the group consisting of *Leuconostoc* spp., *Bifidobacterium* ssp, *Lactococcus lactis, Lactococcus cremoris, Lactobacillus acidophilus, Lactobacillus casei, Lactobacillus kefir, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sake, Lactobacillus reuteri, Lactobacillus lactis, Lactobacillus delbreuckii, Lactobacillus plantarum,* and *Streptococcus thermophilus.* It is particularly preferred that bacteria in the bacteria-containing concentrate belong to one of the above species.

The bacteria-containing concentrate to by dried by use of the improved freeze-drying process optionally contains one or more additives, such as a cryo protectant and/or a stabilizer as defined herein, which preferably has been added after an optional washing process.

The invention also provides dry bacteria-containing products that are obtainable by the improved freeze-drying process disclosed herein. Preferably, this bacterial product comprises from $10^9$ to $10^{13}$ cfu/g LAB cells.

Another aspect of the invention relates to a process for optimizing a freeze drying procedure by improving the storage stability of a freeze dried bacteria-containing product obtained from a bacteria-containing concentrate, the process comprising
  i) preparing a sample of the frozen bacteria-containing concentrate (which optionally contains one or more additives, such as a cryo protectant and/or a stabilizer) and measuring the melting point,
  ii) calculating the sublimation temperature if the existing freeze drying pressure which has hitherto been used for freeze-drying the concentrate is used,
  iii) adjusting the freeze drying pressure to a pressure which will provide a sublimation temperature which is at least 10° C. above the melting point of the frozen bacteria-containing concentrate, and
  iii) freeze drying the bacteria-containing concentrate at a pressure which is at least the adjusted freeze-drying pressure until a freeze dried bacteria-containing product having a desired $a_w$ is obtained from the bacteria-containing concentrate.

The bacteria-containing concentrate in the processes according to the present invention is preferably a LAB-containing concentrate. Such a bacteria-containing concentrate may comprise a bacteria selected from the group consisting of *Acetobacter, Bifidobacterium, Carnobacterium, Enterococcus, Lactococcus, Lactobacillus, Leuconostoc, Pediococcus, Oenococcus, Propionibacterium,* and *Streptococcus.*

More specifically, the bacteria-containing concentrate may comprise at least one strain of a LAB genus, preferably selected from the group consisting of *Lactococcus, Lactobacillus, Leuconostoc, Carnobacterium, Pediococcus,* and *Streptococcus* and more preferably at least one strain of a species selected from the group consisting of *Leuconostoc* spp., *Bifidobacterium* ssp, *Lactococcus lactis, Lactococcus cremoris, Lactobacillus acidophilus, Lactobacillus casei, Lactobacillus kefir, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sake, Lactobacillus reuteri, Lactobacillus lactis, Lactobacillus delbreuckii, Lactobacillus plantarum,* and *Streptococcus thermophilus.*

In presently preferred embodiments the bacteria are of a strain selected from the group consisting of BB-12® that was deposited with the German Collection of Microorganisms and Cell Cultures (DSMZ) under the accession no. DSM15954, BB-12® free that was deposited with the German Collection of Microorganisms and Cell Cultures (DSMZ) under the accession no. DSM17281, LA-5® that was deposited with the German Collection of Microorganisms and Cell Cultures (DSMZ) under the accession no. DSM13241, *Streptococcus thermophilus* ST6008 that was deposited with the German Collection of Microorganisms and Cell Cultures (DSMZ) under the accession no. DSM18111, *Lactobacillus rhamnosus* LGG® that was deposited with the American Tissue type Collection Center under the accession no. ATCC53103, ST-4895 that was deposited with the German Collection of Microorganisms and Cell Cultures (DSMZ) under the accession no. DSM19242 and *Lactococcus lactis* R-607-1 that was deposited with the German Collection of Microorganisms and Cell Cultures (DSMZ) under the accession no. DSM21404, and/or mutants or variants thereof.

In the present context, the term "mutant" should be understood as a strain derived from a mother strain by means of e.g. genetic engineering, radiation, UV light, and/or chemical treatment and/or other methods that induce changes in the genome. It is preferred that the mutant is a functionally equivalent mutant, e.g. a mutant that has substantially the same, or improved, properties as the mother strain. Such a mutant can be used in the processes according to the present invention. Especially, the term "mutant" refers to a strain obtained by subjecting a strain to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood as containing one mutagenization step followed by a screening/selection step), but it is presently preferred that no more than 20, or no more than 10, or no more than 5 treatments (or screening/selection steps) are carried out. In a presently preferred mutant, less that 5%, or less than 1% or even less than 0.1% of the nucleotides in the bacterial genome have been shifted with another nucleotide, or deleted, compared to the mother strain. In a further aspect, the invention relates to a method for predicting whether a change in the freeze-drying pressure used for production of a freeze dried bacteria-containing product from a bacteria-containing concentrate will have a negative effect on the storage stability of the freeze dried bacteria-containing product obtained from the bacteria-containing concentrate, the method comprising
  i) preparing a sample of the frozen bacteria-containing concentrate and measuring the melting point,
  ii) calculating the sublimation temperature if the change in the freeze drying pressure for production of the product is implemented, and
  iii) calculating whether the changed pressure will provide a sublimation temperature which is at least 10° C. above the melting point of the frozen bacteria-containing concentrate.

In a yet further aspect, the present invention relates to a method for predicting whether a change of bacterial species, fermentation procedure, possible washing, concentration factor, nature or amount of cryo protectant and/or stabilizer of a freeze dried bacteria-containing concentrate will have a negative effect on the storage stability of a freeze dried bacteria-containing product obtained from the bacteria-containing concentrate, the method comprising i) preparing a sample of the frozen bacteria-containing concentrate with the desired changes and measuring the melting point, ii) calculating the sublimation temperature if the freeze drying pressure which has hitherto been used for freeze-drying the bacteria-containing concentrate is used, and iii) calculating whether the changed frozen bacteria-containing concentrate will have a melting point which is at least 10° C. below the calculated sublimation temperature.

If the contemplated change is predicted to have a negative effect on the storage stability of a freeze dried bacteria-containing product obtained from the bacteria-containing concentrate, the above method can be repeated so that it is ensured that only changes which will have a positive effect on the storage stability of a freeze dried bacteria-containing concentrate are implemented.

The present invention also relates to a bacteria-containing product obtainable by the processes of the invention. Such a product may have a bacteria concentration from about $10^9$ to about $10^{13}$ cfu/g. The bacteria-containing products of the invention can be distinguished by their shininess when viewed in a microscope. Also, the density of the products obtainable by the processes of the invention may be increased as an indication of micro collapse.

In a preferred embodiment the bacteria-containing product according to the invention has been produced by freeze drying a bacteria-containing concentrate at a pressure in a range of 0.2-1.2 mBar, such as 0.3-0.9 mBar, e.g. in the range of 0.35-0.75 mBar, preferably in the range of 0.35 to 0.5 mBar.

The products obtainable by the processes of the invention have a high storage stability which can e.g. be measured by storing the product for two months in a closed bag at 25° C. and 60% RH. Preferably, the log loss after two months of storage in a closed bag at 25° C. and 60% RH is in the range of 0 to 0.5, such as in the range of 0 to 0.25.

The products find use in various applications, including, but not limited to food production, feed production, dietary supplements, pharmaceutical production (e.g. as active ingredient in health beneficial probiotic products), etc. As indicated above, the present invention finds use in providing storage stable products of any suitable bacteria.

As indicated above, a process of the present invention provides means to obtain products having the desired concentration of viable bacteria also after storage. The activity level of the bacteria concentrates is directly linked to the number of viable bacteria. In some embodiments, the activity of the bacteria (i.e., the microbial activity level) is determined by assessing the amount of metabolite(s) the culture produces over a given time period and utilizing a specific type of substrate. For example, for LAB, it is possible to determine the activity level by continuously recording the pH for a given period of time, as the pH of a LAB culture is directly linked to the concentration of viable bacteria. In some embodiments, comparing the recorded pH measurement to an expected theoretical pH value based on the assumption that all of the bacteria in the culture are viable, provides the concentration and activity level of the suspension. Thus, if the measured pH is close to the theoretical value, the bacterial population has undergone limited activity loss during the process.

Definitions

Unless defined otherwise herein, all technical and scientific terms used herein have the same meaning as commonly understood by one of ordinary skill in the art to which this invention pertains. Although any process and materials similar or equivalent to those described herein find use in the practice of the present invention, the preferred process and materials are described herein. Accordingly, the terms defined immediately below are more fully described by reference to the specification as a whole. It is to be understood that the present invention is not limited to the particular methodology, protocols, and reagents described, as these may vary, depending upon the context in which they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. Furthermore, the citation of any document is not to be construed as an admission that it is prior art with respect to the present invention.

A "washing step" as used herein refers a process step in which the bacteria-containing concentrates are admixed with an aqueous solution. Thus, a washing step normally comprises the addition of an aqueous solution to a bacteria-containing concentrate according to the invention. A washing step may additionally comprise removal of a part of the previously added aqueous solution, such as e.g. by centrifugation or filtration. Washing steps in the sense of the present invention may be carried out successively, e.g. by several successive addition and removal steps in a continuous flow process (see below).

The "water activity" $a_w$ as used herein is defined as the vapor pressure of water in the substance (e.g. the bacteria-containing concentrate of the invention), divided by the vapor pressure of pure water at the same temperature. The skilled person is aware of numerous methods to determine the water activity of a given substance. For example, $a_w$ may be determined by measuring the vapor pressure in the substance and comparison of this vapor pressure with that of water at the same temperature.

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful LAB are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of the strict anaerobic bacteria, bifidobacteria, i.e. *Bifidobacterium* spp., are generally included in the group of LAB. These are frequently used as food cultures alone or in combination with other LAB.

Preferably, the LAB are LAB selected from the group consisting of: LAB belonging to genus *Lactobacillus*, such as *Lactobacillus helveticus, Lactobacillus delbruekii* subsp. *bulgaricus, Lactobacillus fermentum, Lactobacillus salivarius* or *Lactobacillus rhamnosus*; LAB belonging to genus *Lactococcus*, such as *Lactococcus lactis*; LAB belonging to genus *Streptococcus*, such as *Streptococcus thermophilus*; LAB belonging to genus *Leuconostoc*, such as *Leuconostoc lactis* or *L. mesenteroides*; LAB belonging to genus *Bifidobacterium*, such as *Bifidobacterium longum, Bifidobacterium animalis*, or *Bifidobacterium breve*; LAB belonging to genus *Propionibacterium*; LAB belonging to genus *Enterococcus*, such as *Enterococcus faecum*; and LAB belonging to genus *Pediococcus*.

Even more preferably, the LAB are LAB selected from the group consisting of:
*Lactobacillus acidophilus, Lactobacillus rhamnosus, Bifidobacterium animalis, Streptococcus thermophilus* and *Lactococcus lactis*.

"Fermentation" means the conversion of carbohydrates into alcohols or acids through the action of bacteria. Preferably, fermentation in the methods of the invention comprises conversion of lactose to lactic acid. Fermentation processes to be used are well known and the person of skill in the art will know how to select suitable process conditions, such as temperature, pH, oxygen, amount and characteristics of bacteria(s) and process time. Obviously, fermentation conditions are selected so as to support the achievement of the present invention, i.e. to produce (or propagate) bacteria.

A "concentrate" as used herein is a bacteria containing culture that has been concentrated, i.e. the relative number of bacteria has been increased by decreasing the overall volume of the culture, e.g. by removing liquid.

LAB, including bacteria of the species *Lactobacillus* and *Bifidobacterium* are commonly used as probiotic cultures in foods such as fermented milks, yoghurts and cheese, as well as dietary supplements where the probiotic is in the form of a dried product.

A "cryoprotectant" is defined herein as a substance used to protect bacteria cells from damage during freezing, freeze-drying and thawing as well as during storage. The cryoprotectant may be any additive as long as it protects cells from damage during freezing, freeze-drying, thawing and storage. Examples of cryoprotectants include, but are not limited to, sugars (e.g. sucrose, fructose, trehalose), polyalcohols (e.g. glycerol, sorbitol, mannitol), polysaccharides (e.g. celluloses, starch, gums, maltodextrin), polyethers (e.g. polypropylene glycol, polyethylene glycol, polybutylene glycol), antioxidants (e.g. natural antioxidants, such as ascorbic acid, beta-carotene, vitamin E, glutathione, or chemical antioxidants), oils (e.g. rapeseed oil, sunflower oil, olive oil), surfactants (e.g. Tween 20, Tween 80, fatty acids), fats, peptones (e.g. soy peptones, wheat peptone, whey peptone), tryptones, vitamins, minerals (e.g. iron, manganese, zinc), hydrolysates (e.g. protein hydrolysates such as whey powder, malt extract, soy, casein hydrolysate), amino acids, peptides, proteins, nucleic acids, nucleotides, nucleobases (e.g. cytosine, guanine, adenine, thymine, uracil, xanthine, hypoxanthine, inosine, inositol), yeast extracts (e.g. yeast extracts of *Saccharomyces* spp., *Kluyveromyces* spp., or *Torula* spp.), beef extract, growth factors, and lipids. Other examples of cryoprotectants are disclosed in WO2012088261 and WO2012076665 which are incorporated herein by reference. The addition of a cryoprotectant in a process of the invention may be done by mixing a solid cryoprotectant with the bacteria concentrate for a sufficient time period at a suitable temperature.

The term "active" (bacterial) cells as used herein refers to the number of viable cells. The amount of active, i.e. viable, cells may be specified in any unit or measure that is commonly used in the art. For example, the amount of active cells may be given in the number of viable cells or colony forming units (cfu) per gram sample.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

LEGENDS TO FIGURES

FIG. 1. CultureR-607-1: Comparison of drying times between mild (A) and aggressive conditions (B-D). A (5° C., 0.3 mBar); B (50° C., 0.5 mBar); C (50° C., 0.70 mBar); D (50° C., 0.95 mBar)

Figure 2:
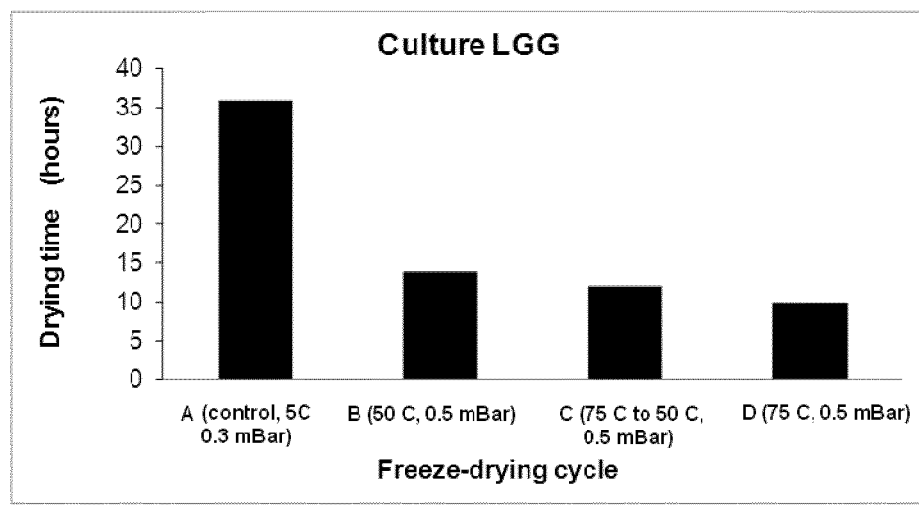

FIG. 2. Culture LGG®: Comparison of drying times between mild (A) and aggressive conditions (B-D). A (5° C., 0.3 mBar); B (50° C., 0.5 mBar); C (75° C.→50° C., 0.5 mBar); D (75° C., 0.5 mBar)

Figure 3:
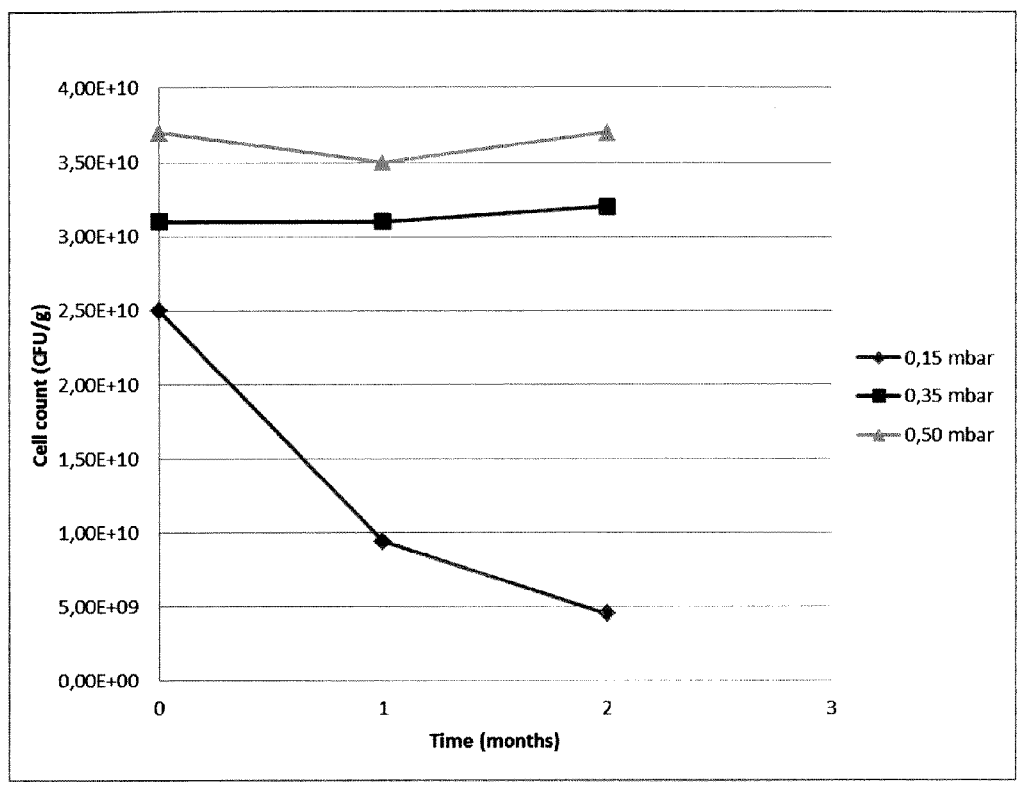

FIG. 3. Comparison of cell counts (cfu/g) of unwashed LGG® dried at different pressures (0.15 mbar, 0.35 mbar and 0.5 mbar) and kept in closed bags for up to 2 months at 25° C. and 60% RH.

Figure 4:
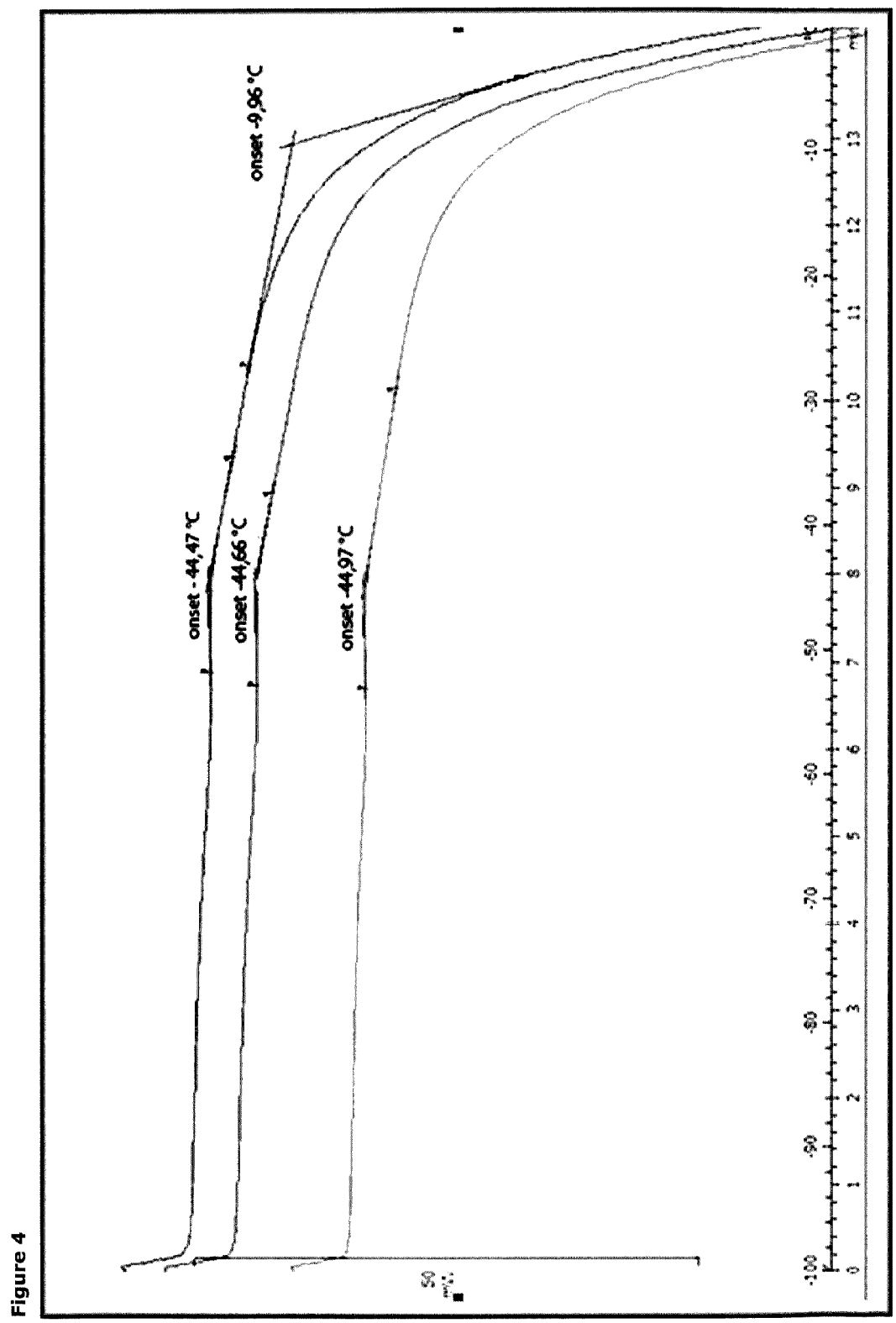

FIG. 4. Melting points of three PFD samples of unwashed LGG® measured on DSC (Differential Scanning Calorimeter) using a DSC 822 Mettler Toledo.

FIG. 5. Steam table (Saturation Condition)

EXAMPLES

Example 1. *Lactococcus Lactis*, R-607-1: Comparison of Product Quality when Freeze-Dried Under Mild and Aggressive Conditions. Effect of High Pressure (0.5-0.95 mBar)

*Lactococcus lactis*, R-607-1 ® with deposit accession number DSM21404 was cultivated in 700 liters MRS. The bacteria in the fermentation broth were concentrated by centrifugation using a centrifuge CSA-6 Westfalia. After centrifugation, the bacterial concentrate was mixed with cryoprotective solution (300 g to 1000 g cell concentrate). Afterwards the bacterial suspension was frozen with liquid nitrogen in the form of pellets (i.e. PFD). The cryoprotective solution consisted of skim milk (14%), monosodium glutamate (6%) and water (80%). The frozen pellets of the bacterial suspension are called pre-freeze-dried product (i.e. PFD). Pre-freeze-dried product (PFD) in the form of frozen pellets (i.e. PFD) with a size of 1 to 5 mm in diameter was used for the freeze-drying trials carried out in the pilot scale described below. The PFD was kept at −50° C. until being freeze-dried.

The freeze-drying was performed in a Hetosicc freeze dryer, CD-10-1, Heto Lab equipment, Heto-Holten A/S, Allerod, Denmark.

The freeze-dryer can operate at pressures in the range of 0.2-2 mBar and is equipped with a heating plates that operates in the range of −40 to +80° C. The condenser operates with an average temperature of −60° C. The amount of material required is between 0 and 10 kg. The freeze-dryer has 6 heating plates designed for Radiant drying and a supporting rack for the trays. The supporting rack for the trays is suspended in a weighing cell (see Atlas Pilot Freeze-drying Plant-RAY™, NIRO, DK). The weighing device is connected to a computer which allows the recording of the mass, i.e. the change in weight during drying due to removal of water, thereby assuring an accurate process control. The drying trays are located between the heating plates by hanging on the rack. Therefore, a maximum of 5 levels of trays can be positioned as the number of heating plates is 6. In this study, 2 trays made of anodised aluminium 470×250×35 mm, were positioned per level, so that in total 10 trays were present in the freeze-drying cabinet (2 trays per level×5 levels=10 trays).

Frozen pellets (PFD) of R-607-1 with a mass of 10 kg were put on the drying trays and afterwards placed in the freeze-drying chamber and dried with 4 different freeze-drying (FD) cycles as indicated below. Freeze-drying (FD) cycle A was a control cycle, i.e. a so-called mild cycle, with a constant heating plate temperature and a constant chamber pressure during the drying of 5° C. and 0.3 mBar, respectively. The other freeze-drying cycles (B, C and D) were carried out using more aggressive drying conditions. A higher pressure of 0.5, 0.7 and 0.95 mBar was applied for FD cycle B, C and D, respectively. The heating plate temperature was also increased from 5 to 50° C. Both pressure and heating plate temperature were kept constant during the drying process (B, C and D).

The end of the drying was reached when stable weight during the drying was reached, and the product temperature was not higher than 35° C.

The following freeze-drying cycles were used:

TABLE 1

| Freeze-drying cycle | Pressure mBar | Heating plate temperature ° C. |
|---|---|---|
| A (Control) | 0.3 | 5° C. |
| B | 0.5 | 50° C. |
| C | 0.7 | 50° C. |
| D | 0.95 | 50° C. |

The water activity ($a_w$) of freeze-dried products was measured immediately after freeze-drying. Water activity ($a_w$) was measured at room temperature using an Rotronic HYGROMETER AwVC (Totronic Instrument Corp., Huntington, N.Y., USA.

The acidification activity in the freeze-dried culture was measured according to the International standard ISO 26323:2009 (IDF 213: 2009): "Milk products—Determination of the acidification activity of dairy cultures by continuous pH measurement (CpH)".

Acidification activity is qualified by the following parameters:

$t_a$: The time it takes to start acidifying the standardized milk, i.e. the time in which the pH drops 0.08 pH units from the initial pH. The time to is measured in minutes from the time of inoculation, t=0.

pH-6h: The pH that is reached after 6 hours at 30° C. for this particular starter culture.

The higher to and pH-6h are, the longer the latency phase and, thus, the lower the acidification activity (Fernanda et al. 2004).

The following categorization was used for the evaluation of the appearance of the freeze-dried product after freeze-drying:

0 refers to products similar to the reference, i.e. normal pellet shape
1 refers to product with a less normal pellet shape
2 refers to product with bad pellet shape
3 refers to product with complete loss of pellet shape Results The aim of the present study was to investigate the effect of aggressive freeze-drying conditions (high pressure) on the quality of freeze-dried products of R-607-1. Examination was done by comparison of both water activity ($a_w$) and acidification activity ($t_a$, pH-6h) of freeze-dried products obtained by aggressive (B-D) and mild (A) FD cycles (see table above). The mild drying (A, reference drying) was carried out with a constant heating plate temperature of 5° C. and with a constant chamber pressure of 0.3 mBar. For the aggressive dryings (B-D), the pressure was increased from 0.3 mBar (A) to 0.5, 0.7 and 0.95 mBar, respectively for the cycles B, C and D. The heating plate temperature was also increased from 5 to 50° C., but it was kept the same for the three cycles B, C and D. Both pressure and heating plate temperature were kept constant during the drying process (A, B, C and D).

No significant difference was observed in acidification activity of FD products when dried with the mild (A) and aggressive freeze-drying conditions (B-D). The time $t_a$ was 91 min for the product obtained with the mild FD cycle compared to a to of 93-97 min for the FD products generated with the more aggressive cycles (B-D). Aggressive FD cycles (B-D) also resulted in a product with a pH-6h value in the same range (4.9-5) to that of the mild FD cycle (pH-6h of 4.9).

Moreover, taking the precision of the analysis into consideration (ISO 26323:2009), the acidification activity of the FD products was not significantly different when the FD product was obtained by the mild cycle or by the aggressive FD cycles. Thus, it can be concluded that aggressive drying at pressure in the range of 0.5-0.95 mBar exerts no detrimental effect on the acidification activity of R-607-1.

Evaluation of freeze-dried products normally also includes the observation of the product appearance after freeze-drying because one of the desired characteristic is to avoid changes in the freeze-dried product appearance. The product appearance after freeze-drying with aggressive drying cycles (B-D) was assessed by visual comparison to a reference freeze-dried product which was obtained by drying with the mild FD cycle (A). No difference in products appearance was observed (Table 2). The fact that the FD product appearance and characteristics were not changed by the aggressive drying procedures (B-D) was also confirmed by a low value of water activity ($a_w$=0.03-0.05) of these FD products. This value was comparable to that of the FD product obtained by the mild drying cycle (A) (0.03) (Table 1).

Despite the fact that no significant differences between acidification activity and $a_w$ of FD products dried under aggressive or mild FD conditions were observed, a significant difference in the drying time was seen (FIG. 1). More aggressive drying cycles (B-D) resulted in approximately 3 times shorter drying times of between 11 and 14.5 h compared to 36 h for the mild FD cycle (A). Thus, the more aggressive cycles result in a much more efficient drying process, especially with regard to the energy costs and the productivity.

The main conclusions from the results presented in Example 1, which was performed with the culture R-607-1, are:

Product quality and performance of the products dried under aggressive conditions (0.5-0.95 mBar and 50° C.) were indistinguishable from those of product dried under 'mild' conditions (0.3 mBar and 5° C.).

No significant difference was observed in acidification activity ($t_a$ and pH-6h) of FD products when dried with the mild and aggressive freeze-drying conditions.

All freeze-dried products from the aggressive dryings were well dried and reached significantly lower water activity of less than 0.05 as compared to 0.03 for that of the mild drying.

No difference in product appearance was seen when comparing FD products obtained by the aggressive drying processes as compared to that obtained by a mild drying process.

Aggressive drying processes resulted in an approximately 3 times shorter drying time compared with that of the mild drying. This results in a much more efficient drying process, especially regarding the energy costs and productivity.

TABLE 2

Culture R-607-1: Comparison of product quality when freeze-dried under mild (A) and aggressive conditions (B-D) with respect to acidification activity ($t_a$, ph-6h), water activity ($a_w$) and product appearance.

| FD Cycle | FD Pressure (mBar) | pH-6h | $t_a$ | $a_w$ | Product appearance after freeze-drying |
|---|---|---|---|---|---|
| A | 0.3 | 4.9 | 91 | 0.03 | 0 |
| B | 0.5 | 4.9 | 93 | 0.03 | 0 |
| C | 0.7 | 5.0 | 94 | 0.05 | 0 |
| D | 0.95 | 5.0 | 97 | 0.05 | 0 |

A (5° C., 0.3 mBar);
B (50° C., 0.5 mBar);
C (50° C., 0.70 mBar);
D (50° C., 0.95 mBar)

Example 2. *Lactobacillus rhamnosus* LGG®: Comparison of Product Quality when Freeze-Dried Under Mild and Aggressive Conditions. Effect of High Temperature (50-75° C.)

*Lactobacillus rhamnosus* (ATCC53103) was cultivated in 700 liters MRS. The bacteria in the fermentation broth were concentrated by centrifugation using a centrifuge CSA-6 Westfalia. After centrifugation, the bacterial concentrate was mixed with cryoprotective solution (300 g to 1000 g cell concentrate). Afterwards, bacterial suspension was frozen with liquid nitrogen in the form of pellets (i.e. PFD). The cryoprotective solution consisted of skim milk (14%), monosodium glutamate (6%) and water (80%). The frozen pellets of the bacterial suspension are called pre-freeze-dried product (i.e. PFD). Pre-freeze dried product (PFD) in the form of frozen pellets (i.e. PFD) with sizes of 1 to 5 mm in diameter were used. The PFD was kept at −50° C. until being freeze-dried. The freeze-drying was carried out as described in Example 1 with four different freeze-drying (FD) cycles as described below. Freeze-drying (FD) cycle A was a control cycle, i.e. a so-called mild cycle with a constant heating plate temperature and constant chamber pressure during the drying process of 5° C. and 0.3 mBar, respectively. For the aggressive dryings (B-D), the pressure was increased from 0.3 mBar (A) to 0.5 mBar and kept constant during the drying. The heating plate temperature was also increased from 5° C. to a constant temperature of 50° C. and 75° C., respectively, for drying cycles B and D. For cycle C the plate temperature was decreased from 75 to 50° C. after 45% water removal.

TABLE 3

| Freeze-drying cycle | Pressure mBar | Heating plate temperature ° C. | Comments |
|---|---|---|---|
| A (Control) | 0.3 | 5° C. | |
| B | 0.5 | 50° C. | |
| C | 0.5 | 75° C. | Heating plate temperature is lowered to +50° C. after 45% water is removed |
| D | 0.5 | 75° C. | |

The water activity ($a_w$) of freeze-dried products was measured immediately after freeze-drying. Water activity ($a_w$) was measured at room temperature using an Rotronic HYGROMETER AwVC (Totronic Instrument Corp., Huntington, N.Y., USA.

The number of viable cells after freeze-drying and after storage test was determined as colony forming units (CFU) as described by Palmfeldt and Hahn-Hägerdal (2000), Int J Food Microbiol, 55(1-3):235-8. The following categorization was used for evaluation of the appearance of the freeze-dried product after freeze-drying:

0 refers to products similar to the reference, i.e. normal pellet shape
1 refers to product with a less normal pellet shape
2 refers to product with bad pellet shape
3 refers to product with complete loss of pellet shape Results The aim of the present study was to investigate the effect of aggressive freeze-drying conditions (high heating plate temperature) on the survival of freeze-dried *Lactobacillus rhamnosus* LGG®. Examination was done by comparison of viable cells (CFU) after freeze-drying of products that were freeze-dried with the mild cycle (A; 5° C. and 0.3 mBar) with products that were freeze-dried with the aggressive FD cycles (B-D; 50-75° C. and 0.5 mbar). The results are summarized in Table 4.

No significant difference was seen in viable cell count after freeze-drying (CFU) when increasing the heating plate temperature from 5° C. (A) to 50° C. (B) and 75° C. (C and D). Moreover, no visual structural change occurred for FD product when the heating plate temperature was increased from 5° C. to 75° C.

In addition, the stability of the product, i.e. the cell survival, was also studied during storage for 3 weeks in open bags at 30° C. and 30% RH (Table 4). Surprisingly, the mild FD conditions (A; heating plate temperature of 5° C. and pressure of 0.3 mBar) affect the cell survival negatively during storage. This FD (A) cycle resulted in the highest cell loss, and therefore, in the lowest viable cell count of 10.8 (log CFU/g) compared to that of 11.5 (log CFU/g) for drying cycle B, and 11-11.1 (log CFU/g) for drying cycles C and D, respectively. The results were also confirmed by flow cytometry (data not shown). Thus, it can be concluded that aggressive drying cycles (B-D) with a heating plate temperature of 50 and 75° C. results in FD product with higher cell viability during storage compared to the mild FD conditions (A) with a heating plate temperature of 5° C.

Also, no visual change in the pellet structure was seen when the product was freeze-dried under high temperatures of 50 and 75° C. (B-D) as compared with a low temperature of 5° C. (A) (Table 4). The fact that there was no change in the pellet structure of the FD products that underwent aggressive drying cycles (B-D) was also confirmed by the rather low water activity of the FD product of less than 0.03, which was also below the Limit of Detection (LOD) of 0.03 for the equipment.

In addition, the more aggressive drying cycles (B-D) resulted in 3 times shorter drying times of 10-14.5 h compared with that of 36 h for the mild FD cycle (A) (FIG. 2). Thus, these were much more efficient drying processes, especially with regard to the energy cost and productivity.

The main conclusions from the results presented in Example 2 that were performed with the culture LGG® are the following:
  Aggressive drying cycles (50 and/or 75° C. and 0.5 mBar) resulted in FD products with a higher cell viability after storage compared with the mild FD conditions (5° C. and 0.3 mBar), although the products showed a comparable viable cell count after freeze-drying (CFU).
  No difference in products appearance was seen when comparing FD products obtained by aggressive drying cycles (50; 75° C. and 0.5 mBar) compared with that of the mild drying cycle (5° C. and 0.3 mBar).
  Freeze-dried products from the aggressive drying cycles were well dried. They reached the same water activity of less than 0.03 as those products of the mild drying. This was also below the Limit of Detection (LOD) of 0.03 for the equipment.
  Aggressive drying cycles resulted in approximately 3 times shorter drying time as compared with that of the mild drying cycle, which results in much more efficient drying processes, especially regarding the energy costs and the productivity.

Example 3

Investigation of *Lactobacillus rhamnosus* LGG®

It was surprisingly experienced that the storage stability of freeze dried (FD) *Lactobacillus rhamnosus* LGG® (ATCC53103) is dependent on the pressure used in the freeze drying profile. The storage stability of unwashed LGG® dried at different pressures (0.15 mbar, 0.35 mbar and 0.5 mbar) when kept in closed bags for up to 2 months at 25° C. and 60% RH is shown in FIG. 2. The temperature profile of the drying was identical for the three samples (65° C. gradually lowered to 32° C.). From FIG. 3 it appears that the storage stability of the *Lactobacillus rhamnosus* LGG® freeze dried at 0.15 mbar is much lower than the storage stability of the *Lactobacillus rhamnosus* LGG® freeze dried at 0.35 mbar or 0.5 mbar.

In order to get an explanation on the differences in storage stability the melting points of the pre-freeze dried product (PFD) was measured (FIG. 4), and the physical appearance of the freeze dried (FD) products were investigated by microscopy using a Olympus SZX9 (Table 5).

TABLE 5

Physical characteristics of LGG ® dried at different pressure

| Sample | FD Pressure | Density (g/ml) | Appearance | Microscopy |
|---|---|---|---|---|
| 1 | 0.15 mbar | 0.158 | Large, white granulates, easy to crush | Porous mat surface |
| 2 | 0.35 mbar | 0.224 | Smaller, yellow, harder | Shiny surface |
| 3 | 0.50 mbar | 0.252 | Smaller, yellow, harder | Shiny surface |

The melting points of three PFD samples were measured on DSC (Differential Scanning Calorimeter) using a DSC 822 Mettler Toledo (FIG. 4). The only differences in the three samples are that the concentrates are from three different fermentations (same fermentation procedure). After harvest the concentrates were added the same amount of cryo additives. This means that theoretically there should be no difference in the three samples. As expected, the melting points were approximately the same for the three samples (−44.47° C., −44.66° C. and −44.97° C., respectively).

TABLE 4

Culture LGG ®: Comparison of the product quality of products that were freeze-dried under mild (A) or aggressive conditions (B-D) with regard to the water activity ($a_w$), product appearance and cell survival (CFU) after freeze-drying and 3 weeks storage at 30° C. and 30% RH.

| | | | Cell viability | | | Product |
|---|---|---|---|---|---|---|
| FD Profile | Temperature-Heating plates (° C.) | Water activity aw | Start: after FD Log CFU/g | After 3 weeks storage Log CFU/g | Cell loss after storage Log loss CFU/g | appearance after freeze-drying |
| A (Control) | 5 | 0.03 | 11.6 | 10.8 | 0.8 | 0 |
| B | 50 | 0.03 | 11.5 | 11.5 | 0.0 | 0 |
| C | 75→50 | 0.03 | 11.5 | 11.1 | 0.4 | 0 |
| D | 75 | 0.03 | 11.3 | 11.0 | 0.3 | 0 |

A (5° C., 0.3 mBar);
B (50° C., 0.5 mBar);
C (75° C.→50° C., 0.5 mBar);
D (75° C., 0.5 mBar)

TABLE 6

Sublimation temperature at different pressures

| Freeze drying pressure | Corresponding temperature |
|---|---|
| 0.5 mbar | −27.4° C. |
| 0.35 mbar | −31° C. |
| 0.15 mbar | −40° C. |

When comparing the melting points (FIG. 4) with the sublimation temperatures (Table 6) and the stability data (FIG. 3), it can be seen that a large difference between the sublimation temperature and the melting point leads to an increased stability. It is contemplated that the explanation on the difference in storage stability is that freeze drying above melting point leads to local melting, encapsulation, a shiny structure and better stability.

Observations with L. Reuteri Protectis

Trials with L Reuteri where the fermentate was concentrated differently but freeze dried using the same freeze drying profile were performed. In two of the trials the fermentate was concentrated with a high concentration factor, in three trials the fermentate was concentrated with a low concentration factor and in another trial the concentration factor was in between. In the case with a high concentration factor the concentrate contained a lower content of fermentation remains whereas the concentrate contained a higher amount of fermentation remains in the trials where low concentration factor was used. The fermentation remains is primarily lactate which is known to decrease the melting point of the PFD.

In Table 7 is shown the observations of the six different freeze dried products produced from concentrate with different concentration factors. The products were kept in closed bags at 25° C. for 8 months with no humidity control. It appears from the table that the log loss during storage is low for the samples with the low concentration factor. The fact that the 3 samples produced with a low concentration factor have a shiny appearance (micro collapse) fits into the theory that some melting results in a kind of coating which protects the culture during storage. As mentioned above the increased content of lactate in the samples produced with concentrate with the lowest degree of concentration will have a higher melting point.

It is worth mentioning that the water activity is low for all the six samples which mean that the difference in storage stability is not due to differences in water activities.

TABLE 7

| No. | Concentration factor | Log loss during storage | Microscopy |
|---|---|---|---|
| 1 | High | 2.3 | Mat surface |
| 2 | High | 1.6 | Mat surface |
| 3 | Medium | 1.0 | Mat surface |
| 4 | Low | 0.8 | Shiny surface |
| 5 | Low | 1.0 | Shiny surface |
| 6 | Low | 0.4 | Shiny surface |

Example 5

Investigation of Lactobacillus reuteri RC-14®

The RC-14 (ATCC 55845) was fermented by standard fermentation procedure. The concentrate as well as the spent medium was collected for further processing. The spent medium was added in formulation 2 in order to simulate poor concentration factor of the culture. The spent medium consists mainly of lactate which has a rather low $T_g$ value (−60° C.).

The cryo additive used in the trial was sucrose, sodium ascorbate and Glucidex IT12 where the main component is sucrose. The cryo additives were dissolved in tab water and sterilized by heat treatment. The different formulations are shown in Table 8, the cfu/g after storage for 3 months in Table 9 and the visual appearance in Table 10.

TABLE 8

Formulation and freeze drying scheme.

| Trial No. | Concentrate gram | Gram cryo mixture | gram spent medium | Freeze drying 0.3 mbar | Freeze drying 0.4 mbar | Freeze drying 0.5 mbar |
|---|---|---|---|---|---|---|
| 1 | 1000 | 475 | 0 | X | | X |
| 2 | 1000 | 475 | 250 | X | X | X |

The products are kept in closed alu-pouches at +25° C. and 60% relative humidity, the samples are analysed after 3 months.

TABLE 9

CFU/g after storage for 3 months at 25° C. in closed alu bags

| Trial No | 0.3 mbar | 0.4 mbar | 0.5 mbar |
|---|---|---|---|
| 1 | 2.1E+11 (100%) | | 2.8E+11 (133%) |
| 2 | 2.3E+11 (100%) | 2.8E+11 (122%) | 3.4E+11 (148%) |

TABLE 10

Visual appearance of the freeze dried products

| Trial No | 0.3 mbar | 0.5 mbar |
|---|---|---|
| 1 | Mat surface, white particles | Shiny surface, yellowish particles |
| 2 | Mat surface, white particles | Shiny surface, yellowish particles |

The product from trial No 2 was the shiniest product which fits very well with a higher degree of melting due to high content of spent medium containing lactate and relatively high content of cryo additive. Product No 2 was also dried at 0.4 mbar. The smaller particles were mat with shiny areas whereas the big particles were shiny.

The above results agree with the theory that some kind of melting during the drying step increases the storage stability.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

PIKAL M. J.; SHAH S. The collapse temperature in freeze drying: dependence on measurement methodology and rate of water removal from the glassy phase. International Journal of Pharmaceutics. 62. 2-3 (1990) 165-186

Schersch et al., Systematic Investigation of the effect of lyophilizate collapse on pharmaceutically relevant proteins I: stability after freeze-drying. J Pharm Sci 2010 May(5):2256-78

WO2012088261

WO2012076665

The invention claimed is:

1. A process for obtaining a freeze-dried bacteria-containing concentrate, comprising:
   (i) preparing a frozen sample of a bacteria-containing concentrate and measuring its melting point,
   (ii) calculating a freeze-drying pressure range that provides a sublimation temperature that is from 10° C. to 20° C. above the melting point of the frozen bacteria-containing concentrate with reference to a saturated steam table, wherein the freeze-drying pressure range is from (a) a pressure corresponding to the sublimation temperature that is 10° C. above the melting point of the frozen bacteria-containing concentrate, as determined with reference to a saturated steam table, to (b) a pressure corresponding to the sublimation temperature that is 20° C. above the melting point of the frozen bacteria-containing concentrate, as determined with reference to a saturated steam table, and
   (iii) freeze-drying the frozen bacteria-containing concentrate at a pressure that is within the calculated freeze-drying pressure range until a freeze-dried bacteria-containing product having a water activity ($a_w$) of no more than 0.2 is obtained, wherein the frozen bacteria-containing concentrate undergoes local melting during freeze-drying.

2. The process of claim 1, wherein the freeze-drying is performed at a pressure that is within the calculated freeze-drying pressure range and is within a range selected from the group consisting of from 0.2 to 2.0 mBar, 0.5 to 2.0 mBar, 0.5 to 1.0 mBar, 0.5 to 0.6 mBar, 0.6 to 0.8 mBar, 0.8 to 1.5 mBar, 0.8 to 1.1 mBar, 0.9 to 1.3 mBar, 0.7 to B 1.1 mBar, 1.0 to 1.9 mBar, 0.4 to 0.6 mBar, and 0.35 to 0.75 mBar.

3. The process of claim 1, wherein the freeze-drying is performed at a pressure that is within the calculated freeze-drying pressure range that is maintained during freeze-drying for a period of time selected from the group consisting of more than 1 hour, more than 2 hours, more than 3 hours, more than 4 hours, and more than 5 hours.

4. The process of claim 1, wherein the freeze-drying is performed until the freeze-dried bacteria-containing product has an $a_w$ of no more than 0.1.

5. The process of claim 1, wherein the bacteria-containing concentrate comprises at least one lactic acid bacteria (LAB) of a genus selected from the group consisting of Lactococcus, Lactobacillus, Leuconostoc, Carnobacterium, Pediococcus, and Streptococcus.

6. The process of claim 1, wherein the bacteria-containing concentrate comprises at least one lactic acid bacteria of a species selected from the group consisting of Leuconostoc spp., Bifidobacterium ssp, Lactococcus lactis, Lactococcus cremoris, Lactobacillus acidophilus, Lactobacillus casei, Lactobacillus kefir, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sake, Lactobacillus reuteri, Lactobacillus lactis, Lactobacillus delbreuckii, Lactobacillus plantarum, and Streptococcus thermophilus.

7. The process of claim 1, wherein the number of bacteria in the bacteria-containing concentrate is selected from the group consisting of from about $10^8$ to about $10^{13}$ cfu/mL, from about $10^9$ to about $10^{13}$ cfu/mL, from about $10^9$ to about $10^{12}$ cfu/mL, and from about $10^{10}$ to about $10^{12}$ cfu/ml.

8. The method of claim 1, wherein the calculated freeze-drying pressure provides a sublimation temperature that is from 13° C. to 17° C. above the melting point of the frozen bacteria-containing concentrate.

9. The process of claim 2, wherein the freeze-drying pressure is from 0.5 to 1.0 mBar.

10. The process of claim 2, wherein the freeze-drying pressure is from 0.6 to 0.8 mBar.

11. The process of claim 2, wherein the freeze-drying pressure is from 0.5 to 0.6 mBar.

12. The process of claim 2, wherein the freeze-drying pressure is from 0.8 to 1.5 mBar.

13. The process of claim 2, wherein the freeze-drying pressure is from 0.35 to 0.75 mBar.

14. The process of claim 1, wherein the freeze-drying is performed at a pressure that is within the calculated freeze-drying pressure range that is maintained during freeze-drying for a period of time selected from the group consisting of more than 7 hours, more than 12 hours, more than 18 hours, and more than 24 hours.

15. The process of claim 1, wherein the freeze-drying is performed until the freeze-dried bacteria-containing product has an $a_w$ of no more than 0.15.

16. The process of claim 1, wherein the freeze-drying is performed at a pressure that is within the calculated freeze-drying pressure range and is within a range selected from 0.2-1.2 mBar, 0.3-0.9 mBar, 0.35-0.75 mBar, and 0.35 to 0.5 mBar.

* * * * *